(12) United States Patent
Johansen et al.

(10) Patent No.: US 10,085,953 B2
(45) Date of Patent: Oct. 2, 2018

(54) SKIN CANCER TREATMENT

(71) Applicant: Avexxin AS, Trondheim (NO)

(72) Inventors: Berit Johansen, Trondheim (NO);
Astrid Jullumistro Feuerherm, Trondheim (NO)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 15/360,084

(22) PCT Filed: May 26, 2015

(86) PCT No.: PCT/EP2015/061534
§ 371 (c)(1),
(2) Date: Nov. 23, 2016

(87) PCT Pub. No.: WO2015/181135
PCT Pub. Date: Dec. 3, 2015

(65) Prior Publication Data
US 2017/0119694 A1    May 4, 2017

(30) Foreign Application Priority Data
May 27, 2014    (GB) .................................. 1409363.7

(51) Int. Cl.
*A61K 31/121* (2006.01)
*A61K 9/00* (2006.01)
(52) U.S. Cl.
CPC .......... *A61K 31/121* (2013.01); *A61K 9/0014* (2013.01); *A61K 9/0053* (2013.01)
(58) Field of Classification Search
CPC ..... A61K 31/121; A61K 9/0014; A61K 9/005
See application file for complete search history.

(56) References Cited

U.S. PATENT DOCUMENTS

| 4,670,465 A | 6/1987 | Guzman et al. |
| 2009/0192201 A1 | 7/2009 | Selman-Housein Sosa |
| 2010/0204298 A1 | 8/2010 | Levy |

FOREIGN PATENT DOCUMENTS

| CN | 1678323 A | 10/2005 |
| CN | 103249408 A | 8/2013 |

(Continued)

OTHER PUBLICATIONS

Huwiler et al (British Journal of Pharmacology (2012) 167 1691-1701).*

(Continued)

*Primary Examiner* — Angela C Brown-Pettigrew
(74) *Attorney, Agent, or Firm* — McCarter & English, LLP; Steven G. Davis

(57) ABSTRACT

A compound of formula (I)

$$R\text{-}L\text{-}CO\text{-}X \qquad (I)$$

wherein R is a $C_{10\text{-}24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group or a salt thereof for use in the treatment of skin cancer such as basal cell carcinoma.

17 Claims, 6 Drawing Sheets

(56) References Cited

FOREIGN PATENT DOCUMENTS

| CN | 104968349 | A  | 10/2015 |
|----|-----------|----|---------|
| EP | 0418680   | A2 | 3/1991  |
| EP | 0765661   | A2 | 4/1997  |
| JP | 09-268153 |    | 10/1997 |
| WO | 1997/38688 | A1 | 10/1997 |
| WO | 2000/02561 | A1 | 1/2000  |
| WO | 2002/060535 | A1 | 8/2002 |
| WO | 2003/063878 | A1 | 8/2003 |
| WO | 2006/096579 | A1 | 9/2006 |
| WO | 2006/106438 | A2 | 10/2006 |
| WO | 2008/075366 | A2 | 6/2008 |
| WO | 2008/075978 | A2 | 6/2008 |
| WO | 2009/038671 | A2 | 3/2009 |
| WO | 2010/128401 | A1 | 11/2010 |
| WO | 2010/139482 | A1 | 12/2010 |
| WO | 2011/039365 | A1 | 4/2011 |
| WO | 2011/097276 | A1 | 8/2011 |
| WO | 2012/028688 | A1 | 3/2012 |
| WO | 2014/082960 | A1 | 6/2014 |

OTHER PUBLICATIONS

Albrightson et al., Selective inhibition of 5-lipoxygenase attenuates glomerulonephritis in the rat. Kidney Int. May 1994;45(5):1301-10.
Alexander et al., Arachidonic acid induces ERK activation via Src SH2 domain association with the epidermal growth factor receptor. Kidney Int. May 2006;69(10):1823-32.
Costabile et al., The immunomodulatory effects of novel beta-oxa, beta-thia, and gamma-thia polyunsaturated fatty acids on human T lymphocyte proliferation, cytokine production, and activation of protein kinase C and MAPKs. J Immunol. Jan. 1, 2005;174(1):233-43.
Cybulsky et al., Complement C5b-9 membrane attack complex increases expression of endoplasmic reticulum stress proteins in glomerular epithelial cells. J Biol Chem. Nov. 1, 2002;277(44):41342-51.
Flock et al., Syntheses of some polyunsaturated sulfur- and oxygen-containing fatty acids related to eicosapentaenoic and docosahexaenoic acids. Acta Chem Scand. Jun. 1999;53(6):436-45.
Holmeide et al., Syntheses okf some polyunsaturated trifluoromethyl ketones as potential phospholipase A2 inhibitors. J Chem Soc Perkins Trans 1. 2000;1(14)2271-2276.
Ingber et al., A novel treatment of contactdermatitis by topical application of phospholipase A2 inhibitor: a double-blind placebo-controlled pilot study. Int J Immunopathol Pharmacol. Jan.-Mar. 2007;20(1):191-5.
Johannesdottir et al., Nonsteroidal anti-inflammatory drugs and the risk of skin cancer: a population-based case-control study. Cancer. Oct. 1, 2012;118(19):4768-76.
Liu et al., EGFR signaling is required for TGF-beta 1 mediated COX-2 induction in human bronchial epithelial cells. Am J Respir Cell Mol Biol. Nov. 2007;37(5):578-88.
Matsuzawa et al., Activation of cytosolic phospholipase A2alpha by epidermal growth factor (EGF) and phorbol ester in HeLa cells: different effects of inhibitors for EGF receptor, protein kinase C, Src, and C-Raf. J Pharmacol Sci. Oct. 2009;111(2):182-92.
Rodriguez et al., Hyperosmotic stress induces phosphorylation of cytosolic phospholipase A(2) in HaCaT cells by an epidermal growth factor receptor-mediated process. Cell Signal. Oct. 2002;14(10):839-48.
Sakaguchi et al., Truncation of annexin A1 is a regulatory lever for linking epidermal growth factor signaling with cytosolic phospholipase A2 in normal and malignant squamous epithelial cells. J Biol Chem. Dec. 7, 2007;282(49):35679-86.
Schalkwijk et al., Maximal epidermal growth-factor-induced cytosolic phospholipase A2 activation in vivo requires phosphorylation followed by an increased intracellular calcium concentration. Biochem J. Jan. 1, 1996;313 ( Pt 1):91-6.
Scuderi et al., Expression of Ca(2+)-independent and Ca(2+)-dependent phospholipases A(2) and cyclooxygenases in human melanocytes and malignant melanoma cell lines. Biochim Biophys Acta. Oct. 2008;1781(10):635-42.
Sommerfelt et al., Cytosolic phospholipase A2 regulates TNF-induced production of joint destructive effectors in synoviocytes. PLoS One. Dec. 12, 2013;8(12):e83555. 8 pages.
Thommesen et al., Selective inhibitors of cytosolic or secretory phospholipase A2 block TNF-induced activation of transcription factor nuclear factor-kappa B and expression of ICAM-1. J Immunol. Oct. 1, 1988;161(7):3421-30.
Yan et al., Cytosolic Phospholipase A2 is Involved in Epidermal Growth Factor and Fetal Bovine Serum-induced Proliferation in Hela Cells. Chinese Doctoral Dissertation & Masters Theses. 68 pages (2005).

\* cited by examiner

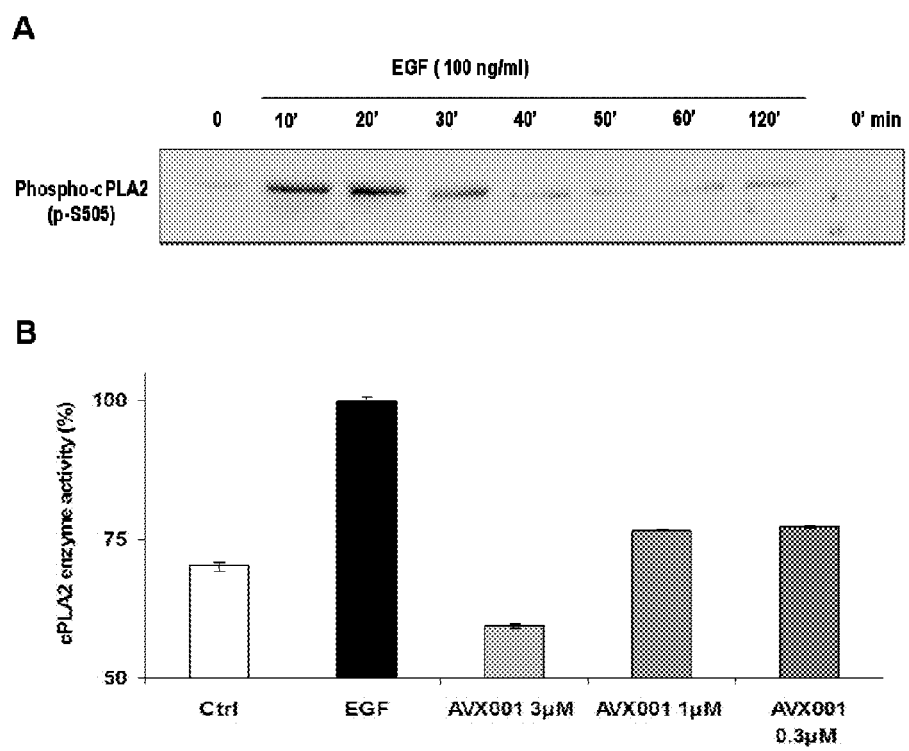
Figure 1A/B.

SKIN CANCER TREATMENT

CROSS-REFERENCES TO RELATED APPLICATIONS

This application is a 35 U.S.C. § 371 U.S. national entry of International Application PCT/EP2015/061534 (WO 2015/181135 A1) having an International filing date of May 26, 2015, which claims under 35 U.S.C. § 119 the benefit of United Kingdom Patent Application No. 1409363.7, filed May 27, 2014. The entire contents of both applications are incorporated herein by reference in their entirety.

This invention relates to the use of certain polyunsaturated long-chain ketones for the treatment of skin cancer such as basal cell carcinoma and in particular to ketones carrying electron withdrawing substituents alpha to the carbonyl functionality in such treatment. The invention also relates to methods of treating skin cancer in patients comprising administration of the compounds of the invention to the patient, ideally topically.

BACKGROUND

Basal cell carcinoma is a common, non-melanoma skin cancer, originating in the basal stem cells of the epidermis. The sun-exposed areas of the head and neck are the most commonly involved sites. Basal cell carcinoma (BCC) predominantly affects Caucasians and is very uncommon in dark-skinned races. BCC is the most common cancer in Europe, Australia and the USA and is showing a worldwide increase in incidence. The most significant aetiological factors appear to be genetic predisposition and exposure to ultraviolet (UV) radiation.

At the moment surgery and radiotherapy appear to be the most effective treatments for BCC, with surgery showing the lowest failure rates. There is only limited evidence of the effectiveness of other treatment modalities compared with surgery, e.g. topical chemotherapy (Imiquimod and Fluoroacil 5% creams). The present inventors therefore sought alternative and/or combinatorial treatments for this condition.

It has been observed that treatment with non-steroid anti-inflammatory drugs (NSAIDS) that target the arachidonyl cascade may reduce cancer progression (Johannesdottir, S. A., et al., Nonsteroidal anti-inflammatory drugs and the risk of skin cancer: a population-based case-control study. Cancer, 2012. 118(19): p. 4768-76; Gonzalez-Periz, A. and J. Claria, New approaches to the modulation of the cyclooxygenase-2 and 5-lipoxygenase pathways. Curr Top Med Chem, 2007. 7(3): p. 297-309).

The present inventors postulate that cytosolic phospholipase A2 group IVa (cPLA2α) enzyme may be involved in the pathogenesis of basal cell carcinoma and other related cancers.

The phospholipases A2 enzymes are a group of lipases that by hydrolysis release unsaturated fatty acids from the sn2 position of membrane phospholipids. Once released, the fatty acids are converted by various enzymes into biologically important signalling molecules. Cytosolic group IVa PLA2 (cPLA2α) is pivotal in inflammation; it is activated by intracellular calcium and by phosphorylation in response to stimuli such as pro-inflammatory cytokines and mitogenic growth factors. cPLA2α is selective for AA-containing acyl chains in vitro, and is considered a central enzyme in AA-derived eicosanoid production. Release of arachidonate initiates the arachidonate cascade leading to the synthesis of eicosanoids such as prostaglandins. Eicosanoids are important in a variety of physiological processes and play a central role in inflammation. Elevated levels of arachidonic acid, eicosanoids and other bioactive lipid mediators are reported in inflammatory dermatoses.

The present inventors also realise that a chronic inflammatory microenvironment is now recognized as a hallmark of cancer, promoting the progression of malignancy, including initiation, growth, angiogenesis, invasion and metastasis.

Of the pro-inflammatory mediators, lipid autocoids such as platelet activating factor, lysophosphatidic acid, prostaglandins and leukotrienes, with their specific receptors and pathways, have been shown to play a critical role in cancer initiation and progression. Hence, bioactive lipids may represent a link between inflammation and cancer.

It is therefore possible that inhibition of the cPLA2α enzyme, the limiting factor for arachidonic acid and lysophospholipid release and availability, should have potential in reducing the inflammatory events promoting aberrant, cancerous basal cell activity due to reduced production of bioactive lipids such as LTB4 and PGE2, in basal cell carcinoma and other related cancers.

Holmeide and Skattebøl reported in 2000 that several structurally different compounds are reported as inhibitors of cPLA2α in vitro (Journal of the chemical society-Perkin transactions, 2000. 1(14): p. 2271-2276). The compounds tested were based around (all-Z)-eicosa-5,8,11,14-,17-pentaenoic acid (EPA) and (all-Z)-docosa-4,7,10,13,16,19-hexaenoic acid (DHA).

In recent publications we validated the Perkins Transactions paper finding of in vitro target efficacy and furthermore show potent cellular anti-inflammatory effects in both mesangial and synovial cells (Huwiler, A., et al., British Journal of Pharmacology, 2012. 167(8): p. 1691-1701; Sommerfelt, R. M., et al., Cytosolic Phospholipase A2 Regulates TNF-Induced Production of Joint Destructive Effectors in Synoviocytes. PLoS ONE, 2013. 8(12): p. e83555).

The treatment of cancer however is complex and the person skilled in the art appreciates that to target cancer successfully requires more than just cPLA2 inhibition.

The pleiotropic epidermal growth factor (EGF) and its receptors (EGFR, HER2, HER3, HER4) are recognized to have pivotal roles in various solid tumours and the EGF pathway is commonly targeted in cancer treatment. In the epidermis, EGFR is predominantly expressed in the basal layer, with increased expression in basal-cell carcinoma relative to normal skin. Furthermore, the phenomenon of EGFR receptor transactivation by bioactive lipids binding to their G-protein coupled receptors (GPCRs) adds to the complexity of EGFR dependent carcinogenic events.

An association between cPLA2α, the arachidonate cascade and EGF/EGFRs is described in several model systems and types of cancer; e.g. human cervical carcinoma HeLa cells, in lung epithelial cells, in the kidney and in squamous cell carcinoma keratinocytes (Matsuzawa, Y., et al., J Pharmacol Sci, 2009. 111(2): p. 182-92; Liu, M., et al., American Journal of Respiratory Cell and Molecular Biology, 2007. 37(5): p. 578-88; Alexander, L. D., et al., Kidney International, 2006. 69(10): p. 1823-32; Johnson, F. M., et al., Journal of Experimental Therapeutics and Oncology, 2004. 4(4): p. 317-25).

As outlined, EGFR and COX/LOX are accepted treatment targets in cancer, including BCC. However, there are no reports on the effects of targeting the common interactor enzyme cPLA2α in an effort to modulate and normalize these aberrant signalling events in cancer. The biochemistry here is therefore complex and unpredictable.

The present inventors have surprisingly found that:

1) EGF activates cPLA2α in keratinocytes in a time-dependent manner;
2) EGF-induced cPLA2α activity is halted by use of certain polyunsaturated ketones in a dose-dependent manner;
3) Use of polyunsaturated ketones such as AVX001 defined herein reduce EGF-meditated keratinocyte proliferation, indicating the rationale to target cPLA2α in BCC and other related cancers.

The compounds proposed for use in this invention have been disclosed before, for example, in EP-A-1469859 but only in the treatment of psoriasis which is a skin condition but is not a form of skin cancer. Psoriasis is an autoimmune induced, chronic disease of skin, characterized by T-cell accumulation, inflammation and hyperproliferation of keratinocytes in epidermis.

Psoriasis has very different biochemistry/immunology than BCC. The compounds have also been suggested, in WO2010/139482, for the treatment of glomerulonephritis or for the treatment of rheumatoid arthritis in WO2012/028688. Again, these uses are far removed from the present application.

The present inventors have now shown experimentally that the compounds of the invention have utility in the treatment of skin cancer through a series of valuable biochemical processes, not limited to cPLA2 inhibition. It is the ability of these compounds to affect multiple biochemical processes that makes them attractive in skin cancer treatment.

SUMMARY OF INVENTION

Thus, viewed from one aspect the invention provides a compound of formula (I)

R-L-CO—X (I)

wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group or a salt thereof for use in the treatment of skin cancer such as basal cell carcinoma.

Viewed from another aspect the invention provides a method of treating skin cancer such as basal cell carcinoma comprising administering to an animal, preferably a mammal, in need thereof, e.g. human, an effective amount of a compound of formula (I):

R-L-CO—X (I)

wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group or a salt thereof.

Viewed from another aspect the invention provides use of a compound of formula (I) or a salt thereof as hereinbefore described for use in the manufacture of a medicament for treating skin cancer such as basal cell carcinoma.

Viewed from another aspect the invention provides a compound of formula (I)

R-L-CO—X (I)

wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group or a salt thereof for use in the treatment of cancer such as basal cell carcinoma.

DETAILED DESCRIPTION

This invention involves the use of compounds of formula (I) or a salt thereof in the treatment of skin cancer such as basal cell carcinoma, squamous cell carcinoma and related conditions. Such related conditions may, in particular, be cancers in which basal cells play an active role.

Cancer

This invention targets skin cancer such as squamous cell carcinoma and in particular basal cell carcinoma. BCCs are abnormal, uncontrolled growths or lesions that arise in the skin's basal cells, which line the deepest layer of the epidermis. BCCs often look like open sores, red patches, pink growths, shiny bumps, or scars. Usually caused by a combination of cumulative UV exposure and intense, occasional UV exposure, BCC can be highly disfiguring if allowed to grow, but almost never spreads (metastasizes) beyond the original tumor site. Only in exceedingly rare cases can BCC spread to other parts of the body and become life-threatening.

There are an estimated 2.8 million cases of BCC diagnosed in the US each year making it the most frequently occurring form of all cancers. The present inventors have realised that the compounds of the invention either alone, mixed with each other or in combination with other BCC therapies, such as radiotherapy, offer a possible new route to the treatment of this common but dangerous condition.

Compounds of the Invention

The invention relies on a compound of formula (I)

R-L-CO—X (I)

wherein R is a $C_{10-24}$ unsaturated hydrocarbon group optionally interrupted by one or more heteroatoms or groups of heteroatoms selected from S, O, N, SO, $SO_2$, said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group or a salt thereof.

The group R preferably comprises 5 to 9 double bonds, preferably 5 or 8 double bonds, e.g. 5 to 7 double bonds such as 5 or 6 double bonds. These bonds should be non-conjugated. It is also preferred if the double bonds do not conjugate with the carbonyl functionality.

The double bonds present in the group R may be in the cis or trans configuration however, it is preferred if the majority

of the double bonds present (i.e. at least 50%) are in the cis configuration. In further advantageous embodiments all the double bonds in the group R are in the cis configuration or all double bonds are in the cis configuration except the double bond nearest the carbonyl group which may be in the trans configuration.

The group R may have between 10 and 24 carbon atoms, preferably 12 to 20 carbon atoms, especially 17 to 19 carbon atoms.

Whilst the R group can be interrupted by at least one heteroatom or group of heteroatoms, this is not preferred and the R group backbone preferably contains only carbon atoms.

The R group may carry up to three substituents, e.g. selected from halo, $C_{1-6}$ alkyl e.g. methyl, $C_{1-6}$ alkoxy. If present, the substituents are preferably non-polar, and small, e.g. a methyl group. It is preferred however, if the R group remains unsubstituted.

The R group is preferably linear. It preferably derives from a natural source such as a long chain fatty acid or ester. In particular, the R group may derive from AA, EPA or DHA.

Thus, viewed from another aspect the invention employs a compound of formula (I')

R-L-CO—X    (I')

wherein R is a $C_{10-24}$ unsubstituted unsaturated hydrocarbon group said hydrocarbon group comprising at least 4 non-conjugated double bonds;

L is a linking group forming a bridge of 1 to 5 atoms between the R group and the carbonyl CO wherein L comprises at least one heteroatom in the backbone of the linking group; and X is an electron withdrawing group or a salt thereof. Ideally R is linear. R is therefore preferably a $C_{10-24}$ polyalkylene chain.

The linking group L provides a bridging group of 1 to 5 backbone atoms, preferably 2 to 4 backbone atoms between the R group and the carbonyl. The atoms in the backbone of the linker may be carbon and/or be heteroatoms such as N, O, S, SO, $SO_2$. The atoms should not form part of a ring and the backbone atoms of the linking group can be substituted with side chains, e.g. with groups such as $C_{1-6}$ alkyl, oxo, alkoxy, or halo.

Preferred components of the linking group are —$CH_2$—, —CH($C_{1-6}$alkyl)-, —N($C_{1-6}$alkyl)-, —NH—, —S—, —O—, —CH═CH—, —CO—, —SO—, —$SO_2$— which can be combined with each other in any (chemically meaningful) order to form the linking group. Thus, by using two methylene groups and an —S— group the linker —$SCH_2CH_2$— is formed. It will be appreciated that at least one component of the linker provides a heteroatom in the backbone.

The linking group L contains at least one heteroatom in the backbone. It is also preferred if the first backbone atom of the linking group attached to the R group is a heteroatom or group of heteroatoms.

It is highly preferred if the linking group L contains at least one —$CH_2$— link in the backbone. Ideally the atoms of the linking group adjacent the carbonyl are —$CH_2$—.

It is preferred that the group R or the group L (depending on the size of the L group) provides a heteroatom or group of heteroatoms positioned α, β, γ, or δ to the carbonyl, preferably β or γ to the carbonyl. Preferably the heteroatom is O, N or S or a sulphur derivative such as SO.

Highly preferred linking groups L therefore are —$NH_2CH_2$—, —NH(Me)$CH_2$—, —$SCH_2$—, —$SOCH_2$—, or —$COCH_2$—

The linking group should not comprise a ring.

Highly preferred linking groups L are $SCH_2$, $NHCH_2$, and N(Me)$CH_2$.

The group X is an electron withdrawing group. Suitable groups in this regard include O—$C_{1-6}$ alkyl, CN, $OCO_2$—$C_{1-6}$ alkyl, phenyl, $CHal_3$, $CHal_2H$, $CHalH_2$ wherein Hal represents a halogen, e. g. fluorine, chlorine, bromine or iodine, preferably fluorine.

In a preferred embodiment the electron withdrawing group is $CHal_3$, especially $CF_3$.

Thus, preferred compounds of formula (I) are those of formula (I')

R—Y1-Y2-CO—X wherein R and X are as hereinbefore defined;

Y1 is selected from O, S, NH, N($C_{1-6}$-alkyl), SO or $SO_2$ and

Y2 is $(CH_2)_n$ or CH($C_{1-6}$ alkyl); or where n is 1 to 3, preferably 1.

Highly preferred compounds for use in the invention are depicted below.

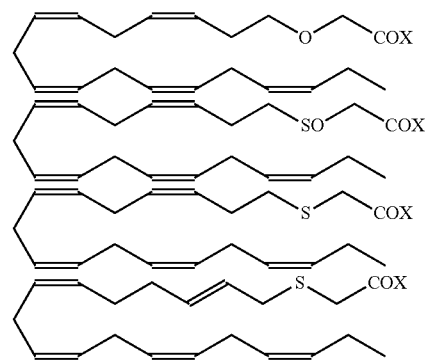

where X is as hereinbefore defined such as $CF_3$.

The following compounds are highly preferred for use in the invention:

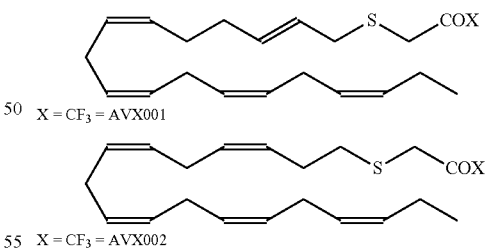

X = $CF_3$ = AVX001

X = $CF_3$ = AVX002

Where possible, the compounds of the invention can be administered in salt, solvate, prodrug or ester form, especially salt form. Preferably however, no such form is used.

Typically, a pharmaceutical acceptable salt may be readily prepared by using a desired acid. The salt may precipitate from solution and be collected by filtration or may be recovered by evaporation of the solvent. For example, an aqueous solution of an acid such as hydrochloric acid may be added to an aqueous suspension of a compound of formula (I) and the resulting mixture evaporated to dryness (lyophilised) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (eg methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts, in particular the tris or bis trifluoroacetate salt and the monoformate salt.

In a further highly preferred embodiment, the compound of the invention is a sulphonium salt. In such a compound, a sulphur atom in the backbone of the molecule, e.g. in the linker group, is functionalised to carry a C1-6-alkyl group. This can be achieved through reaction with an alkyl halide, e.g. methyl iodide. The halide ion forms the counterion of the salt.

In a further preferred embodiment therefore the invention provides a sulphonium salt of a compound of formula (I). Preferably the compound is of formula (VI)

$$RS(C_{1-6}alkyl)CH_2-COX^+Z^-  \quad (VI)$$

where R and X are as hereinbefore defined and Z is a counterion, e.g. halide; e.g. the compound

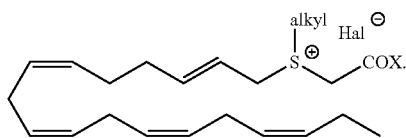

Compounds of formula (I) may be manufactured using known chemical synthetic routes. It is convenient to begin synthesis from the commercially available compounds arachidonic acid (AA), EPA (all-Z-eicosa-5,8,11,14,17-pentaenoic acid) or DHA (all-Z-docosa-4,7,10,13,16,19-hexaenoic acid). Conversion of the acid functionality of these compounds into, for example a —COCF$_3$ group can be achieved readily, e.g. by converting the carboxylic acid into its corresponding acid chloride and reacting the same with trifluoroacetic anhydride in the presence of pyridine.

Introduction of a heteroatom into the carbon chain is also achieved readily. Conveniently, for example, the starting acid is reduced to an alcohol and, if required, converted to the corresponding thiol. The nucleophilic thiol may then be reacted with a group such as BrCH$_2$COCF$_3$ thereby introducing the carbonyl and electron withdrawing species. Complete synthetic protocols may be found in J. Chem. Soc., Perkin Trans 1, 2000, 2271-2276 or J. Immunol., 1998, 161, 3421.

Where the backbone of the molecule contains a nitrogen atom, an alternative synthesis is required. Formation of a polyunsaturated alcohol can be achieved using protocols give in the above Perkin Trans paper. Thereafter, conversion of an alcohol —OH to —NH$_2$ with, for example, phthalimide and subsequent hydrazine reduction allows formation of a —NH$_2$CH$_2$COCF$_3$ group by reaction with trifluoropropyleneoxide (TFPO) and oxidation of the hydroxyl to a ketone. This reaction is shown below.

Methylation of the nitrogen can be effected before this reaction by the formation of an N—BOC group and reduction, e.g. with lithium aluminium hydride. Reaction with TFPO and oxidation yields the linker NMe-CH$_2$.

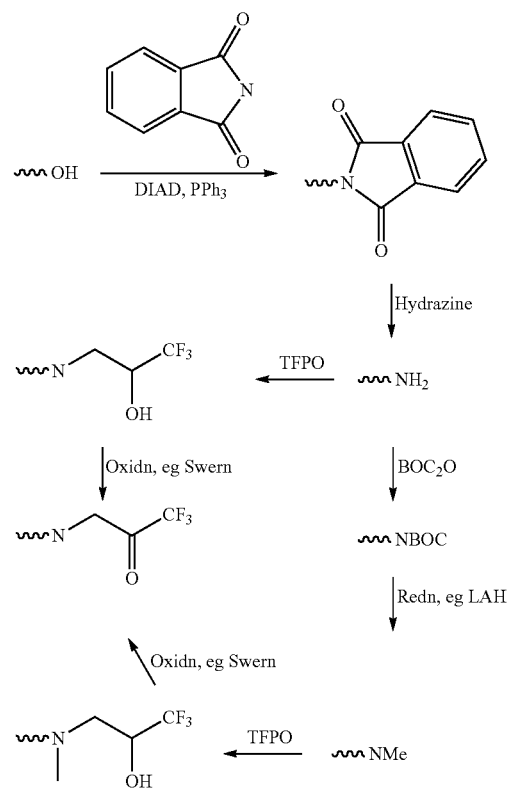

The compounds of the invention are proposed primarily for use in the treatment of, inter alia, skin cancer.

By treating or treatment is meant at least one of:
(i). preventing or delaying the appearance of clinical symptoms of the disease developing in a mammal;
(ii). inhibiting the disease i.e. arresting, reducing or delaying the development of the disease or a relapse thereof or at least one clinical or subclinical symptom thereof, or
(iii). relieving or attenuating one or more of the clinical or subclinical symptoms of the disease.

The benefit to a subject to be treated is either statistically significant or at least perceptible to the patient or to the physician. In general a skilled man can appreciate when "treatment" occurs. It is particularly preferred if the compounds of the invention are used therapeutically, i.e. to treat a condition which has manifested rather than prophylactically. It may be that the compounds of the invention are more effective when used therapeutically than prophylactically.

The compounds of the invention can be used on any animal subject, in particular a mammal and more particularly to a human or an animal serving as a model for a disease (e.g., mouse, monkey, etc.).

In order to treat a disease an effective amount of the active agent needs to be administered to a patient. A "therapeutically effective amount" means the amount of a compound that, when administered to an animal for treating a state, disorder or condition, is sufficient to effect such treatment. The "therapeutically effective amount" will vary depending on the compound, the disease and its severity and the age, weight, physical condition and responsiveness of the subject to be treated and will be ultimately at the discretion of the attendant doctor.

It may be that to treat cancer according to the invention that the compound of formula (I) has to be reapplied at certain intervals. Suitable dosage regimes can be prescribed by a physician.

While it is possible that, for use in the methods of the invention, a compound of formula I may be administered as the bulk substance, it is preferable to present the active ingredient in a pharmaceutical formulation, for example, wherein the agent is in admixture with a pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers are well known in the art. The pharmaceutical compositions may also comprise any suitable binder(s), lubricant(s), suspending agent(s), coating agent(s), and/or solubilizing agent(s) and so on. The compositions can also contain other active components, e.g. other drugs for the treatment of skin cancer.

The active agent of the invention may therefore be combined with steroids or barrier materials (such as zinc oxide).

It will be appreciated that pharmaceutical compositions for use in accordance with the present invention may be in the form of oral, parenteral, transdermal, sublingual, topical, implant, nasal, or enterally administered (or other mucosally administered) suspensions, capsules or tablets, which may be formulated in conventional manner using one or more pharmaceutically acceptable carriers or excipients. The compositions of the invention could also be formulated as nanoparticle formulations.

However, for the treatment of cancer, the compositions of the invention will preferably be administered orally or ideally for skin cancer topically. The compound may therefore be provided in the form of an ointment, cream, salve or gel.

The pharmaceutical compositions of the invention may contain from 0.01 to 99% weight-per volume of the active material.

A therapeutically effective amount of the compound of the present invention can be determined by methods known in the art. The therapeutically effective quantities will depend on the age and on the general physiological condition of the patient, the route of administration and the pharmaceutical formulation used. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

The compounds of the invention may be used to treat cancer in combination with other known pharmaceuticals for said purpose and this forms a further aspect of the invention. In particular, a combination with Imiquimod, 5-Fluorouracil (5-FU) or Erivedge™ (vismodegib) is contemplated.

Alternatively, the compounds of the invention might be used in combination with radiotherapy, cryotherapy, phototherapy, laser therapy or radiation therapy. The invention is described further below with reference to the following non-limiting examples and figures.

DESCRIPTION OF FIGURES

FIG. 1A/B shows that AVX001 reduces EGF-induced cPLA2α activation and AA/OA release in keratinocytes, suggesting that cPLA2α inhibition is a promising treatment strategy for epithelial hyperproliferation and cancer. EGF activates cPLA2α in human keratinocytes as shown by immunoblotting (A) and by cPLA2α in vitro activity assay (B).

In FIG. 2a Arachidonic release assays show that EGF increase AA release by ~35% following one hour of EGF stimulation in keratinocytes and that this increase is completely abrogated by fluoroketones AVX001 (A) and AVX002 (B). # $p<0.04$ vs. untreated control, *$p<0.01$, $p<0.02$, *$p<0.05$. Results shown are mean±SD for from one representative experiment, each experiment was performed in triplicates (n=3). This indicates that cPLA2α inhibition is a promising treatment strategy for epithelial hyperproliferation and cancer.

In FIG. 3a EGF activates post-confluent keratinocytes and leads more cells into S-phase at the expense of G1/G2-M phases. Treatment with cPLA2a inhibitor AVX001 may counteract this entry into S-phase and restrain the resting keratinocytes in G1 phase. Post-confluent cells were serum starved, pretreated with AVX001 (5 μM) for 2 hrs and stimulated with EGF (100 ng/ml) for 24 hrs as described in the Methods section. Results shown are mean±SD for n=6 independent experiments.

One representative histogram shown for each treatment group from 6 independent experiments performed.

Figure 4:
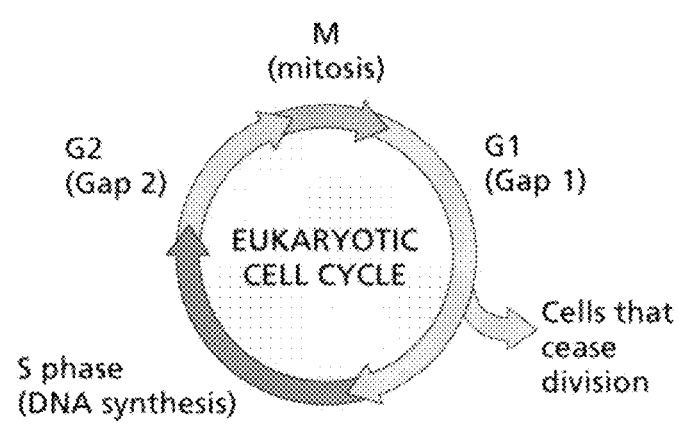

FIG. 4 shows the cycle of S, G2, M and G1.

EXAMPLES

The following compounds were used in the Experiments:

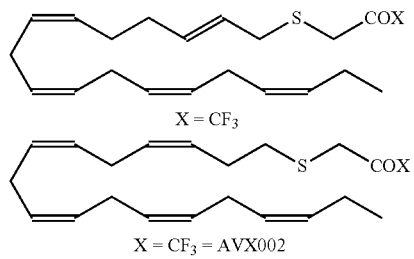

Materials

Recombinant human epidermal growth factor (EGF) was from R&D systems. Phosphate-buffered saline solution (PBS) was from Oxoid. Labelled [5,6,8,9,11,12,14,15-$^3$H]-arachidonic acid, L-α-1-palmitoyl-2-arachidonyl-[arachidonyl-1-$^{14}$C]-phosphatidylcholine and liquid scintillation cocktail Ultima Gold were from NEN Perkin Elmer. Dulbecco's Modified Eagle Medium (DMEM), foetal bovine serum (FBS), fatty acid-free bovine serum albumin (fBSA), dimethyl-sulpfoxide (DMSO), gentamicin, L-glutamine, RNase, propidium iodide (PI) and bromoenol lactone (BEL) and dithiothreitol (DTT) were all from Sigma-Aldrich. Leupeptin and pepstatin were from Roche Molecular Biochemicals. PGE2 ELISA kit was from Cayman Chemicals. Phospho-cPLA2 (Ser505) antibody was from Cell Signal Technology. α-tubulin antibody was from Santa Cruz Biotechnology. Polyclonal goat anti-mouse immunoglobulins horse raddish peroxidase-conjugated secondary antibody was from Dako. Hybond-C nitrocellulose membranes were from GE Healthcare. NuPAGE gel system (10% Bis-Tris gel) was from Invitrogen. SuperSignal® West Femto Maximum Sensivity substrate was from Thermo Scientific. Fluoroketones AVX001 and AVX002 were synthesized and characterized according to Holmeide and Skattebol (Supra) and kindly provided by Dr. Inger Reidun Aukrust and Dr. Marcel Sandberg (Synthetica AS, Norway). Both compounds were stored at −80° C. as 20 mM stock solution in ethanol under argon gas to minimize oxidation.

Cell Culture

The spontaneously immortalized skin keratinocyte cell line HaCaT (kindly provided by Prof. N. Fusenig, Heidelberg, Deutsches Krebsforschungszentrum, Germany) [1] was cultured in DMEM supplemented with 10% (v/v) FBS, 0.3 mg/ml glutamine, and 0.1 mg/ml gentamicin at 37° C. with 5% CO2 in a humidified atmosphere. For release assays, flow cytometry cell cycle analysis and in vitro cPLA2α activity assay, cells were grown in 48 well trays or in 6 well trays, respectively. Cells were cultivated until 2 days post-confluency; serum starved in DMEM/0.5% FBS overnight and processed at day 3 post-confluence to ensure differentiation [2]. Experiments were performed in DMEM/0.5% FBS. Untreated cells without inducing agents were included for unstimulated control. When inhibitors were applied, cells were pretreated for 2 hrs before stimulation with EGF (100 ng/mL).

cPLA2α Enzyme In Vitro Activity Assay

Lysate from stimulated HaCaT keratinocytes was used as the source for cPLA2α enzyme in the in vitro activity assay as described by Wijkander et al [3] with some modifications. HaCaT keratinocytes were serum starved over-night before stimulation with EGF (100 ng/ml) for 1 and 2 hours. Cells were lysed and 200 μg of total protein was analyzed for cPLA2α activity as described [4-7]. Bromoenol lactone (BEL) (25 μM) and dithiothreitol (DTT) (2.36 mM) were included in all reactions to inhibit activity of iPLA2 and sPLA2 [7].

Immunoblotting

Following EGF (100 ng/ml) treatment for the indicated times with or without AVX001 and AVX002 inhibitors, cells were washed in PBS and lysed in buffer containing 50 mM Tris pH 7.5, 150 mM NaCl, 10% glycerol, 0.5% Triton-X-100, 2 mM EDTA, 40 mM β-glycero-phosphate, 100 mM NaF, 200 μM Na3VO4, 10 μg leupeptin, 1 μM pepstatin and 1 mM phenylmethylsulfonyl fluoride. Lysates were cleared by centrifugation, separated by SDS-PAGE and electrophoretically transferred to Hybond-C nitrocellulose membranes (GE Healthcare) using the NuPAGE gel system (10% Bis-Tris gel) from Invitrogen. Membranes were blocked in Tris-buffered saline containing 0.1% Tween 20 and 5% non-fat dry milk for 1 hour at room temperature before incubation with the desired antibodies overnight at 4° C. Following washing three times with Tris-buffered saline containing 20% Tween 20, immunoreactive proteins were detected by horseradish peroxidase-conjugated secondary antibody (1 hour at room temperature) and SuperSignal® West Femto Maximum Sensivity substrate. Blots were analyzed by the BioRad Image Lab software, and target protein band intensities were normalized to α-tubulin.

[3H]-Arachidonic Acid Release Assay

At 2 days post-confluency, HaCaT were labelled for 18 h with $^3$H-AA (0.4 μCi/ml) in DMEM/0.5% FBS. After labelling, the cells were washed twice with phosphate-buffered saline (PBS) containing fatty acid free BSA (2 mg/ml) (fBSA) in order to remove unincorporated radioactivity. After stimulation, the supernatants were cleared of detached cells by centrifugation (13000 rpm, 10 min). The release of $^3$H-AA from the cells was assessed by liquid scintillation counting in a LS 6500 Multi-Purpose Scintillation Counter, Beckman Coulter. Adherent cells were dissolved in 1M NaOH in order to determine incorporated $^3$H-AA in the cells by liquid scintillation counting. The results are given as released $^3$H-AA in the supernatants relative to total $^3$H-AA incorporated into the cells.

Cell Cycle Phase Analysis by Flow Cytometry

Following 24 h treatment with EGF (100 ng/ml) with or without AVX001 (1-5 μM), cells were harvested by routine trypsin detachment and resuspended with ice-cold methanol (−20° C., 100%) for 15 min Methanol-fixated cells were resuspended and incubated with 2 ml RNase (200 μg/ml) for 45 min before nucleic acid staining in 1.5 ml PI (50 μg/ml). After 15 min incubation at room temperature, cell cycle phase distribution was analyzed using a Beckman Coultier Gallios flow cytometer with 20000 cells per sample analyzed. The software Kaluza 1.1 was used for data analysis.

Results

EGF Induced cPLA2α Enzyme Activity in Post-Confluent Keratinocytes is Abrogated by cPLA2α Inhibitor AVX001.

In response to pro-inflammatory stimuli, cPLA2α can be activated by phosphorylation at Ser$^{505}$. In order to investigate if the epidermal growth hormone EGF could activate cPLA2α in keratinocytes, we first performed immunoblotting to assess if cPLA2α was phosphorylated in response to EGF. cPLA2α was not phosphorylated in resting, untreated keratinocytes, whereas EGF evokes a rapid and time-dependent Ser$^{505}$ phosphorylation cycle that peaked at 20 minutes stimulation (FIG. 1A). The increase in phosphorylated cPLA2α in response to EGF indicates that EGF activates cPLA2α. We next wanted to confirm this observation by in vitro cPLA2α activity assay, using cell lysate from HaCaT keratinocytes as the source of cPLA2α. Here, we found that lysates of EGF-stimulated cells displayed a ~30% increase in activity of cPLA2α compared to untreated cells as indicated by increased hydrolysis and release of $^{14}$C-AA from phospatidylcholine visualized by TLC chromatography (FIG. 1B). The increased AA hydrolysis was most prominent following 1 hour of EGF stimulation and declined completely following 4 hours of stimulation. This time-dependent increase in hydrolysis of AA is consistent with the detected preceeding increase in cPLA2α Ser$^{505}$ phosphorylation and confirms that EGF activates cPLA2α in post-confluent HaCaT keratinocytes. Having shown that EGF activates cPLA2α, it was of interest to establish if fluoroketone AVX001 would inhibit AA-hydrolysis. Indeed, AVX001 clearly inhibited AA-hydrolysis, even at 0.3 μM (FIG. 1B). Hence, cPLA2α seem to participate in EGF/EGFR signalling pathways in epithelial cells such as the keratinocytes of the epidermis.

EGF Induced Keratinocyte AA Release is Efficiently Inhibited by AVX001 and AVX002 cPLA2α Inhibitors.

Figure 2A:
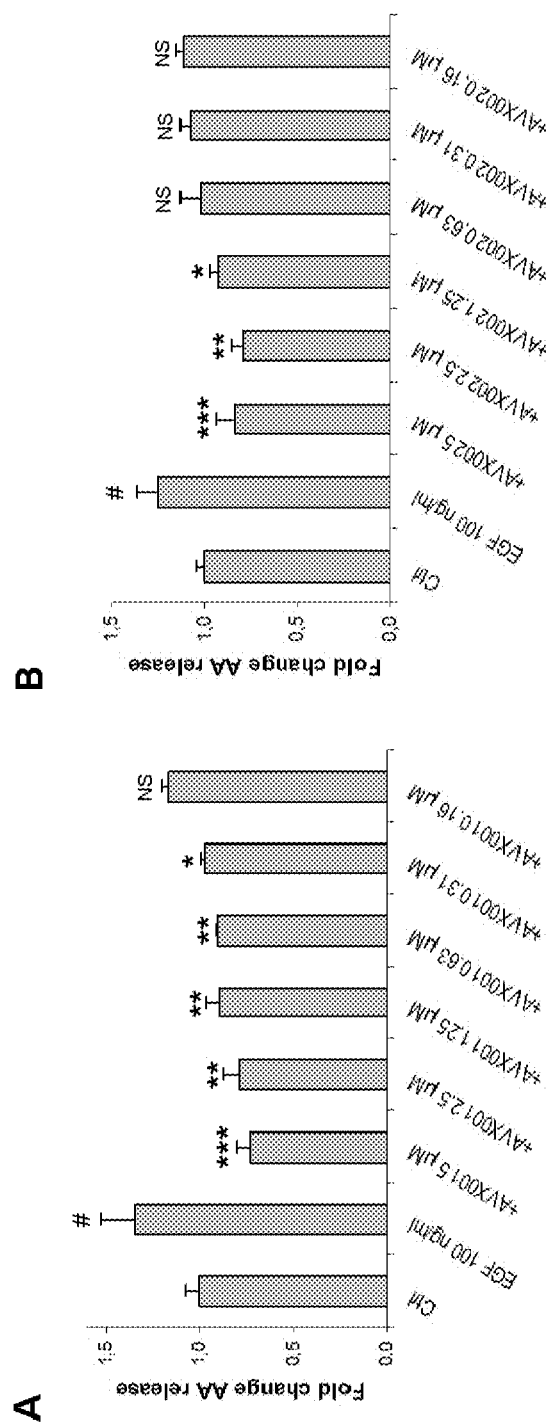
FIG. 2a/2b show that AVX001 reduce EGF-induced cPLA2α activation and AA/OA release in keratinocytes, suggesting that cPLA2α inhibition is a promising treatment strategy for epithelial hyperproliferation and cancer.
Figure 2B:
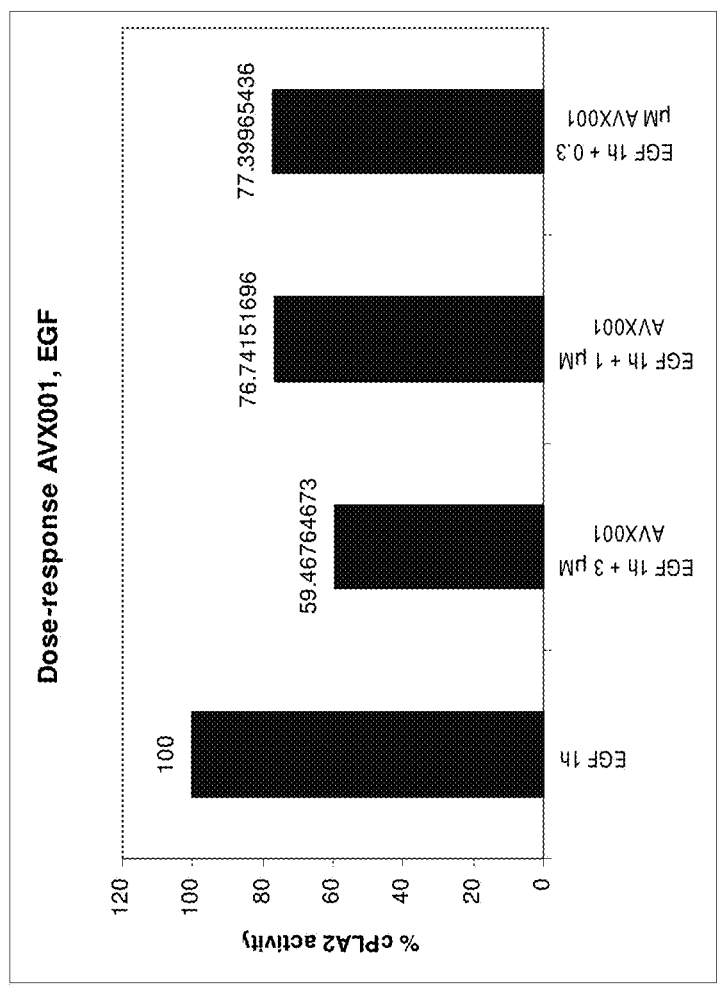

The next step in evaluating the involvement of cPLA2α in EGF/EGFR signalling pathways was to examine if EGF induced AA release in keratinocytes; AA being an important precursor for several mitogenic bioactive lipids. Initial experiments were performed to deduce the ideal experimental conditions (results not shown). In short, we found that EGF induced AA release in a time- and dose-dependent manner; the increase was evident after 20 minutes, peaked at 60 minutes (typically induced a 35% increase) and declined back to normal after 90 minutes, indicating that 1 h stimulation was the ideal EGF exposure time to investigate AA-release. No significant effect was observed for release of $^{14}$C-oleic acid, implicating that other PLA2 isotypes (sPLA2, iPLA2) are not activated or inhibited by EGF. Regarding the dose of EGF, little effect was seen at 10-50 ng/ml, and there was no difference between 100 and 200 ng/ml, hence 100 ng/ml was chosen for the subsequent experiments. Having established the optimal dose and time for EGF treatment, our aim was to investigate the effect of the cPLA2α inhibitors AVX001 and AVX002 on EGF-induced AA-release. We found that AVX001 and AVX002 reduced AA-release to below basal release in a dose-dependent manner, indicating a very strong inhibitory potency for both inhibitors with estimated IC$_{50}$ values in the ~300 nM to 1 μM range (FIG. 2).

EGF Induce a Shift in Cell Cycle Phase Distribution that May be Counteracted by cPLA2α Inhibitor AVX001

Figure 3A:
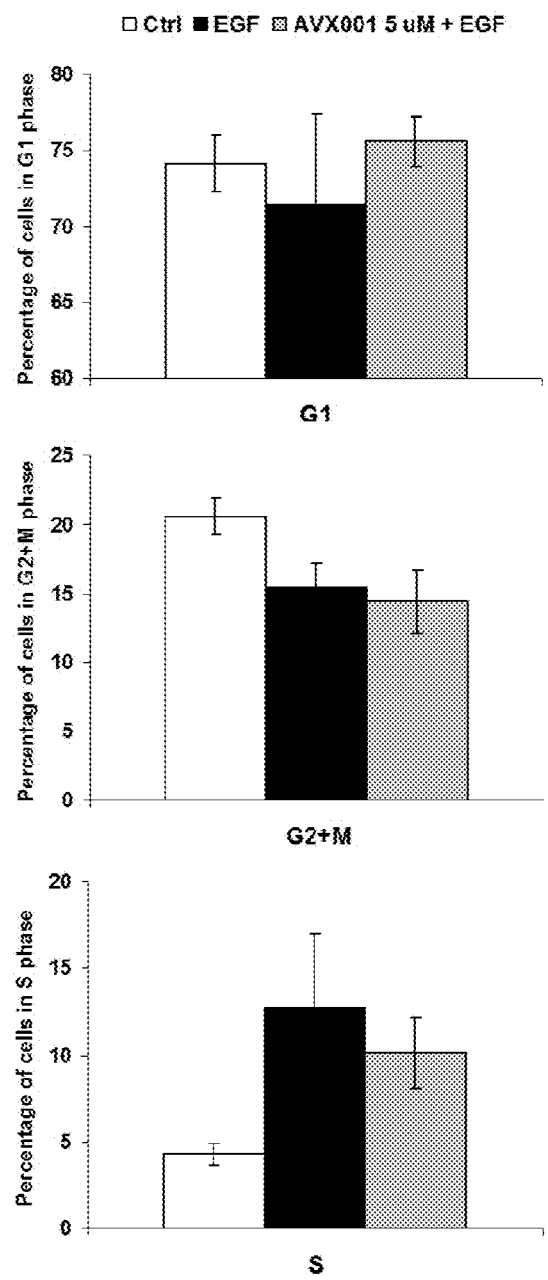
FIG. 3a/b shows that EGF activates post-confluent keratinocytes and leads more cells into S-phase at the expense of G1/G2-M phases. Treatment with cPLA2α inhibitor AVX001 may counteract this entry into S-phase and restrain the resting keratinocytes in G1 phase. Post-confluent cells were serum starved, pretreated with AVX001 (5 μM) for 2 hrs and stimulated with EGF (100 ng/ml) for 24 hrs as described in the methods section.
Figure 3B:
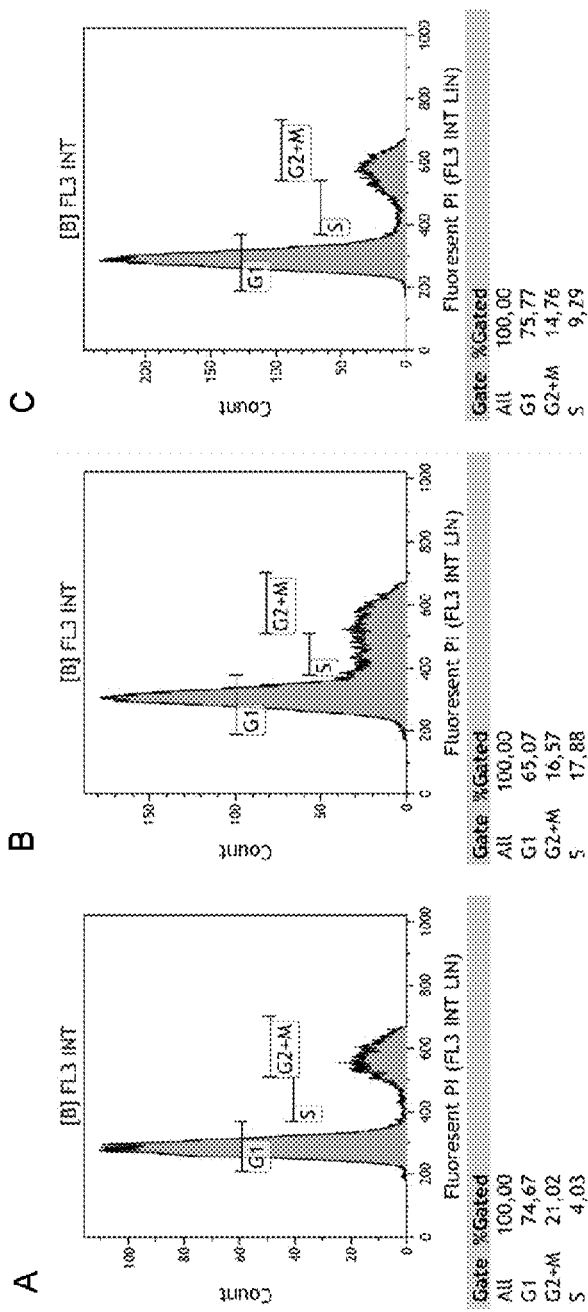
In FIG. 3b, EGF activates post-confluent keratinocytes and leads more cells into S-phase at the expense of G1/G2-M phases. Histograms show cell phase distribution for untreated cells (A), cells treated with EGF (B) and cells treated with both EGF and 5 μM AVX001 (C). Treatment with cPLA2α inhibitor AVX001 may counteract this entry into S-phase and restrain the resting keratinocytes in G1 phase. Post-confluent cells were serum starved, pretreated with AVX001 (5 μM) for 2 hrs and stimulated with EGF (100 ng/ml) for 24 hrs as described in the Methods section.

Having shown that EGF activates cPLA2α in keratinocytes, we next wanted to elucidate if this could be related to mitogenic events. By means of DNA-propidium iodide stain flow cytometry analysis we observed that in response to EGF a fraction of post-confluent cells re-entered cell cycle; less cells were found in G1/G2-M phases and more cells were residing in the S-phase following 24 hrs of EGF treatment (FIG. 3a/b). This shift from resting phase to active, DNA-synthesis phase was in part reversed by the cPLA2α inhibitor AVX001 that was able to restrain most cells in G1 phase.

REFERENCES

1. Boukamp, P., et al., *Normal keratinization in a spontaneously immortalized aneuploid human keratinocyte cell line.* J. Cell Biol., 1988. 106(3): p. 761-771.
2. Jorgensen, K. M., et al., *Platelet activating factor stimulates arachidonic acid release in differentiated keratinocytes via arachidonyl non-selective phospholipase A2.* Arch Dermatol Res, 2010. 302(3): p. 221-7.
3. Wijkander, J. and R. Sundler, *An 100-kDa arachidonate-mobilizing phospholipase A2 in mouse spleen and the macrophage cell line J774.* European Journal of Biochemistry, 1991. 202(3): p. 873-880.
4. Anthonsen, M. W., et al., *Atypical λ/ιPKC Conveys 5-Lipoxygenase/Leukotriene B4-mediated Cross-talk between Phospholipase A2s Regulating NF-κB Activation in Response to Tumor Necrosis Factor-α and Interleukin-1β.* J Biol Chem, 2001. 276(38): p. 35344-35351.
5. Huwiler, A., et al., *The ω3-polyunsaturated fatty acid derivatives AVX001 and AVX002 directly inhibit cytosolic phospholipase A2 and suppress prostaglandin E2 formation in mesangial cells.* Br J Pharmacol, 2012. 168(8): p. 1691-1701.
6. Wijkander, J. and R. Sundler, *An 100-kDa arachidonate-mobilizing phospholipase A2 in mouse spleen and the macrophage cell line J774.* Eur J Biochem, 1991. 202(3): p. 873-880.
7. Lucas, K. K. and E. A. Dennis, *Distinguishing phospholipase A2 types in biological samples by employing group-specific assays in the presence of inhibitors.* Prostaglandins Other Lipid Mediat, 2005. 77(1-4): p. 235-248.

The invention claimed is:

1. A method of treating skin cancer comprising administering to an animal an effective amount of a compound of formula (I'):

R—Y1-Y2-CO—X         (I')

wherein R is a linear unsubstituted $C_{10-24}$ unsaturated hydrocarbon group said hydrocarbon group comprising at least 4 non-conjugated double bonds;
Y1 is selected from O, S, SO or $SO_2$ and
Y2 is ($CH_2$);
n is 1 to 3;
X is $CHal_3$; or a salt thereof.

2. The method of claim 1 wherein said hydrocarbon group R has 5 to 7 double bonds.

3. The method of claim 1 wherein in said hydrocarbon group R no double bond is conjugated with the carbonyl group.

4. The method of claim 1 wherein in said hydrocarbon group R all double bonds are in the cis configuration or wherein in said hydrocarbon group all double bonds are in the cis configuration except the double bond nearest the carbonyl.

5. The method of claim 1 wherein the R group comprises 17 to 19 carbon atoms.

6. The method of claim 1 wherein Y1Y2 is —$SCH_2$—, or —$SOCH_2$—.

7. The method of claim 1 wherein X is $CF_3$.

8. The method of claim 1 wherein said compound of formula (I) has the formula:

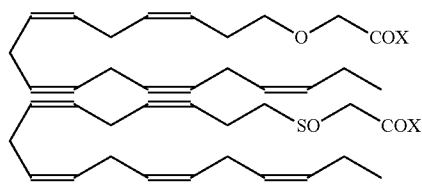

-continued

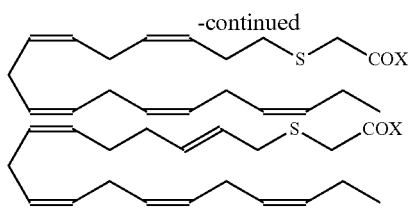

wherein X is CHal₃.

9. The method of claim 8 wherein X is CF₃.

10. The method of claim 1 wherein the compound of formula (I) is

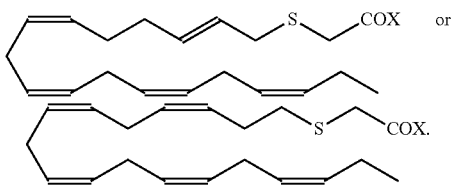

X = CF₃

11. The method of claim 1 wherein the compound of formula (I) is

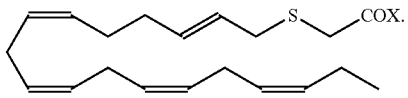

X = CF₃

12. The method of claim 1 wherein the compound of formula (I) is

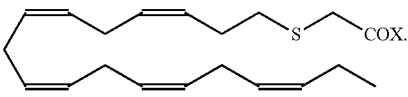

X = CF₃

13. The method of claim 1 wherein the skin cancer is squamous cell carcinoma or basal cell carcinoma.

14. The method of claim 1 wherein the animal has squamous cell carcinoma or basal cell carcinoma.

15. The method of claim 1 wherein the compound is administered orally or topically.

16. The method of claim 1 wherein the animal is a mammal.

17. The method of claim 1 wherein the animal is a human.

* * * * *